United States Patent
Andren et al.

(10) Patent No.: US 12,269,217 B2
(45) Date of Patent: Apr. 8, 2025

(54) BIOPRINTER AND METHOD FOR CALIBRATION OF THE BIOPRINTER

(71) Applicant: Cellink Bioprinting AB, Gothenburg (SE)

(72) Inventors: Anton Andren, Mölndal (SE); Peter Faltpihl, Gothenburg (SE); Erik Sternå, Mölndal (SE); Adam Micha, Gråbo (SE); Ali Cakir, Gothenburg (SE); Hector Martinez, Gothenburg (SE); Erik Gatenholm, Gothenburg (SE)

(73) Assignee: Cellink Bioprinting AB, Gothenburg (SE)

( * ) Notice: Subject to any disclaimer, the term of this patent is extended or adjusted under 35 U.S.C. 154(b) by 179 days.

(21) Appl. No.: 17/922,095

(22) PCT Filed: May 3, 2021

(86) PCT No.: PCT/SE2021/050409
§ 371 (c)(1),
(2) Date: Oct. 28, 2022

(87) PCT Pub. No.: WO2021/230789
PCT Pub. Date: Nov. 18, 2021

(65) Prior Publication Data
US 2023/0166455 A1    Jun. 1, 2023

(30) Foreign Application Priority Data

May 12, 2020   (SE) .................................... 2050555-8

(51) Int. Cl.
*B29C 64/393*   (2017.01)
*B29C 64/112*   (2017.01)
(Continued)

(52) U.S. Cl.
CPC .......... *B29C 64/393* (2017.08); *B29C 64/112* (2017.08); *B29C 64/209* (2017.08);
(Continued)

(58) Field of Classification Search
None
See application file for complete search history.

(56) References Cited

U.S. PATENT DOCUMENTS

2015/0037445 A1   2/2015  Murphy et al.
2017/0146489 A1   5/2017  Redding et al.
(Continued)

FOREIGN PATENT DOCUMENTS

WO   WO 2012/054195 A2   4/2012
WO   WO 2019/178086 A1   9/2019

OTHER PUBLICATIONS

International Search Report and Written Opinion prepared by the European Patent Office, acting as the International Searching Authority, for international application PCT/SE2021/050409 mailed Aug. 26, 2021.
(Continued)

*Primary Examiner* — Galen H Hauth
*Assistant Examiner* — Baileigh Kate Darnell
(74) *Attorney, Agent, or Firm* — McCarter & English, LLP

(57) ABSTRACT

A bioprinter (1) comprising at least one printhead (4a, 4b, 4c) with nozzle (5), a printbed (20) onto which the printhead (4a, 4b, 4c) is arranged to print an ink, an ultrasonic sensor arrangement arranged at the printbed (20), a controller (7) arranged to control movement of the printhead/nozzle (4a, 4b, 4c; 5) and to perform calibration of the printhead/nozzle (4a, 4b, 5 4c; 5) based on information from the ultrasonic sensor arrangement.

6 Claims, 3 Drawing Sheets

(51) Int. Cl.
  *B29C 64/209* (2017.01)
  *B33Y 10/00* (2015.01)
  *B33Y 30/00* (2015.01)
  *B33Y 50/02* (2015.01)
  *C12M 1/42* (2006.01)
  *C12M 3/00* (2006.01)

(52) U.S. Cl.
  CPC ............ *C12M 21/08* (2013.01); *C12M 35/04* (2013.01); *B33Y 10/00* (2014.12); *B33Y 30/00* (2014.12); *B33Y 50/02* (2014.12)

(56) References Cited

U.S. PATENT DOCUMENTS

2017/0355146 A1* 12/2017 Buller ..................... B22F 10/38
2019/0015901 A1    1/2019 Haberland et al.
2020/0346405 A1* 11/2020 Norfolk ............. G06F 11/3013
2020/0406542 A1* 12/2020 Bennett ................ B29C 64/245

OTHER PUBLICATIONS

Swedish Search Report prepared for priority Swedish application SE 2050555-8 mailed Jan. 18, 2021.

\* cited by examiner

BIOPRINTER AND METHOD FOR CALIBRATION OF THE BIOPRINTER

CROSS-REFERENCE TO RELATED APPLICATIONS

This application is the National Stage entry under 35 U.S.C. § 371 of International Application Number PCT/SE2021/050409 filed on May 3, 2021, published on Nov. 18, 2021 under publication number WO 2021/230789 A1, which claims the benefit of priority under 35 U.S.C. § 119 of Swedish patent application number 2050555-8 filed May 12, 2020.

TECHNICAL FIELD

The present disclosure relates to the field of additive manufacturing of biological materials. In particular, the present disclosure relates to a bioprinter and to a method for calibration of the printhead/nozzle in the bioprinter.

BACKGROUND ART

Printing, an additive manufacturing technology, has gained due attention for its ability to spatially control the placement of cells, biomaterials and biological molecules. Consequently, it offers endless possibilities to the future of tissue and organ regeneration, basic research and drug screening. The 3D printer is able to dispense materials while moving in X, Y, and Z directions, which enables the engineering of complex structures from the bottom up.

Moreover, this technology allows the bio-fabrication of biomimetic-shaped 3D structures unique to the target tissue or organ, since it can be combined with CAD/CAM technology using patients' medical images.

An important aspect of a multi-head bioprinter is its ability to precisely print in the same location with all its printheads. During assembly and use, minor deviations in the orientation of the printheads arise, resulting in the position of the end-effector, nozzle end, being offset from its ideal position.

To achieve good quality prints using multiple heads, an accurate means for calibration of the end-effectors is necessary. In the case of the BIO X™ instrument for example, the end effectors must be calibrated with a precision of 20-50 um.

The current method for automatic calibration consists of touching a plastic joystick with the printer nozzles. The method is sub-optimal because of several reasons: the end-effector sometimes misses the joystick; the joystick easily breaks; all nozzles touch the same joystick which might cause cross-contamination. Therefore, a robust method for touch free calibration is needed.

SUMMARY

It is an object of the present invention to provide an improved or at least an alternative bioprinter and a method for calibration of printhead(s)/nozzles(s) in the bioprinter.

According to a first aspect there is provided bioprinter comprising at least one printhead, the printhead being provided with a nozzle, a printbed onto which the printhead is arranged to print an ink, an ultrasonic sensor arrangement arranged at the printbed, said ultrasonic sensor arrangement comprising a first sensor arrangement being arranged to provide a first ultrasound cone extending in a first direction perpendicular to an extension of the nozzle and a second sensor arrangement being arranged to provide a second ultrasound cone extending in a second direction perpendicular to the extension of the nozzle, wherein the first and the second sensor arrangement are arranged to detect when the nozzle has entered its ultrasound cone, the first and second directions preferably being perpendicular to each other. A controller is arranged to control movement of the printhead/nozzle and to perform calibration of the printhead/nozzle, said calibration comprising controlling the printhead/nozzle in accordance with a calibration scheme, and to determine a relation between the nozzle and the first and second ultrasonic cones based on the detections by the first and second sensor arrangements while the nozzle is moving according to the calibration scheme, whereby a calibrated position of the printhead/nozzle at least in the first and second directions and preferably in the direction along the extension of the nozzle can be obtained, and said controller further being arranged to control movement of the printhead/nozzle in accordance with the performed calibration.

The bioprinter may be a biodispenser for dispensing ink.

The first and/or second sensor arrangement may comprise an ultrasonic sensor and at least one solid surface arranged to direct a beam from the sensor forming the cone extending in the first/second direction perpendicular to the extension of the nozzle.

Alternatively, the first and/or second sensor arrangement may comprise an ultrasonic sensor and a curved sound pipe arranged to direct a beam from the sensor forming the cone extending in the first/second direction perpendicular to the extension of the nozzle.

According to a second aspect there is provided a method for calibration of a printhead in a bioprinter, the printhead being provided with a nozzle, the bioprinter further comprising a printbed onto which the printhead is arranged to print an ink, and an ultrasonic sensor arrangement arranged at the printbed, said ultrasonic sensor arrangement comprising a first sensor arrangement being arranged to provide a first ultrasound cone extending in a first direction perpendicular to an extension of the nozzle and a second sensor arrangement being arranged to provide a second ultrasound cone extending in a second direction perpendicular to the extension of the nozzle, wherein the first and the second sensor arrangement detect when the nozzle has entered an ultrasound cone, the first and second directions preferably being perpendicular to each other. The method comprising the steps of controlling the printhead/nozzle in accordance with a calibration scheme and determining a relation between the nozzle and the first and second ultrasonic cones based on the detections by the first and second sensor arrangements when the printhead/nozzle is moving according to the calibration scheme, whereby a calibrated position of the printhead/nozzle at least in the first and second directions and preferably in the direction along the extension of the nozzle can be obtained.

Controlling the nozzle in accordance with a calibration scheme and determining a relation between the nozzle and the first and second ultrasonic cones based on the detections by the first and second sensor arrangements when the nozzle is moving according to the calibration scheme may comprise:

controlling the nozzle to move according to a position determination scheme controlling the nozzle in the second direction in relation to the first ultrasound cone so as to detect by means of the first ultrasonic sensor arrangement the location of the borders of the first ultrasound cone in the second direction, controlling the nozzle to move according to a position determination scheme controlling the nozzle in the first direction in relation to the second ultrasound cone, said position determination scheme being based on the location of the borders of the first ultrasound cone and a spatial relation between the first and the second ultrasonic sensor arrangements, so as to detect by means of the second ultrasonic sensor arrangement the location of the boarders of the second cone in the first direction, whereby the position of the nozzle in the first and second directions can be determined based on the locations of the borders of the first and second ultrasound cones.

Controlling the nozzle in accordance with a calibration scheme and determining a relation between the nozzle and the first and second ultrasonic cones based on the detections by the first and second sensor arrangements when the nozzle is moving according to the calibration scheme may further comprise controlling the nozzle to move according to a position determination scheme controlling the nozzle in the second direction in relation to the first ultrasound cone, said position determining scheme being based at least on the location of the borders of the second ultrasound cone and the spatial relation between the first and second ultrasonic sensor arrangements, so as to detect by means of the first ultrasonic sensor arrangement updated locations of the borders of the first ultrasound cone in the second direction, whereby the position of the nozzle in the first and second directions is determined based on the updated locations of the borders of the first ultrasound cones and the boarders of the second ultrasound cones.

The method may further comprise a step of determining a position of the nozzle in a direction extending substantially along the extension of the nozzle based on the knowledge of the position of the nozzle in the first and second directions.

The method may further comprise controlling the nozzle to a start position outside the first and second ultrasound cones in a direction along the extension of the nozzle, and controlling the nozzle to move from the start position according to a ultrasound cone finding pattern, so as to detects the first ultrasound cone, whereupon control according to the calibration scheme is started.

With the above described bioprinter and method for calibration, a printhead, a plurality of printheads, a multi-head or exchangeable printheads in a bioprinter may be calibrated such that printing in the same location with different printheads at the printbed is possible. Thereby, deviations in the orientation of the printheads and nozzles provided thereon, which may arise during assembly and use and resulting in the position of the nozzle and the nozzle end being offset from its ideal position, may be minimised. The present bioprinter and method providing a robust bioprinter for touch free calibration, an automatic calibration.

DETAILED DESCRIPTION

Printing, an additive manufacturing technology, has gained due attention for its ability to spatially control the placement of cells, biomaterials and biological molecules. Consequently, it offers endless possibilities to the future of tissue and organ regeneration, basic research and drug screening.

The 3D bioprinter/biodispenser is able to dispense materials while moving in X, Y, and Z directions. This enables the engineering of complex constructs from the bottom up. Moreover, this technology allows for bio-fabrication of biomimetic-shaped 3D structures unique to the target tissue or organ, since it can be combined with CAD/CAM technology using patients' medical images.

FIG. 1a discloses an example of a bioprinter/biodispenser 1 according to the present disclosure. The bioprinter 1 can be used for manufacture of three-dimensional engineered biological tissues. The bioprinter may be for use in printing constructs that are suitable for use in any of the applications chosen from: implants in the animal or human body, such as repairing or replacing tissue, topical applications, cosmetic applications, drug test, drug discovery applications or as a disease model, or for other research, investigating or developmental purposes in the pharmaceutical, medical, chemical, personal care, skin care or cosmetic industry or any other industry for which 3D printed constructs may be of use.

The bioprinter 1 comprises a print bed 20. The printbed 20 comprises for example a petri dish. A petri dish is defined as a shallow cylindrical glass or plastic lidded dish used for culturing cells. The printbed 20 comprises in one example a microwell, also known as a microplate. The printbed 20 comprises in one example a glass slide.

Figure 1:
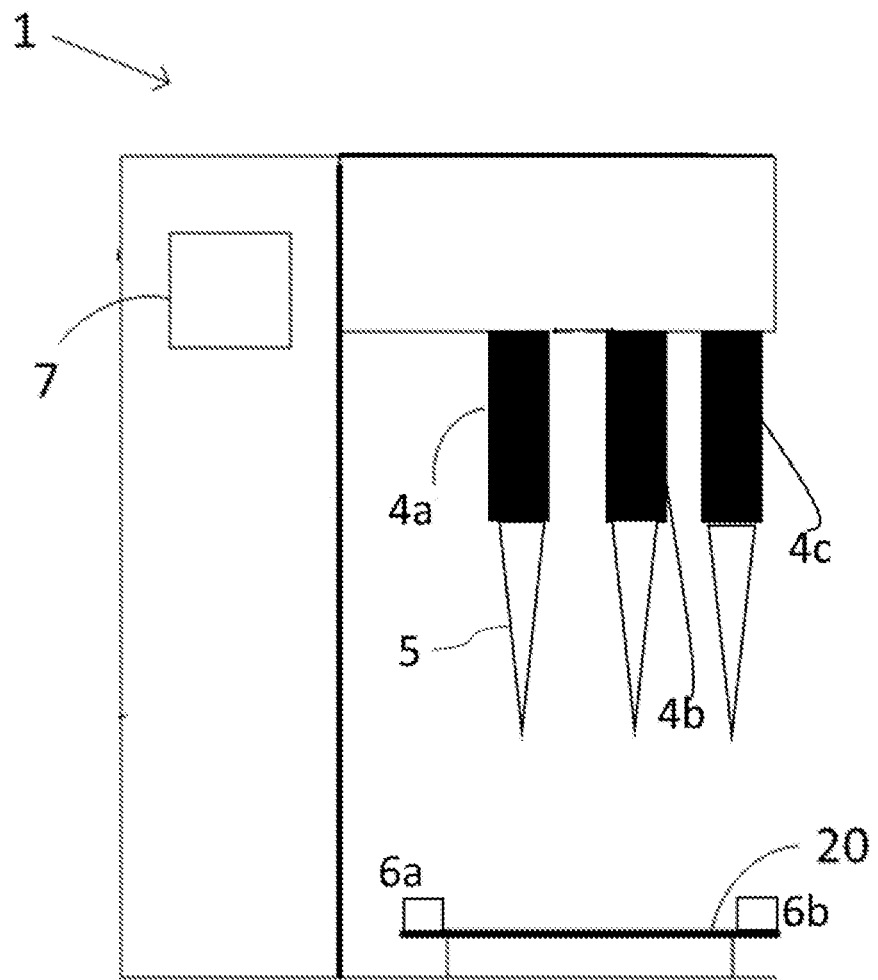
FIG. 1 shows a side view of a bioprinter/biodispenser.

The bioprinter further comprises at least one printhead 4a, 4b, 4c. The bioprinter 1 may comprise one printhead, a multi-head or a plurality of printheads. In FIG. 1 the bioprinter is illustrated with three printheads 4a, 4b, 4c. The printheads may be replaceable. The printheads may be arranged to in turn print an ink, a bioink, on the printbed 20. Examples of printheads include pneumatic extrusion heads, syringe pump heads, inkjet heads, high temperature extrusion heads etc.

The at least one printhead 4a, 4b, 4c is provided with a nozzle 5, which may be demountably arranged on the printhead. The nozzle may be an extrusion needle. The printhead 4a, 4b, 4c and the printbed 20 may be movable in relation to each other. Thereby, the bioprinter is arranged to print a 3D article on the printbed by controlling extrusion through the nozzle 5 by means of an extrusion element and by controlling a relative movement between the printbed and the nozzle/printhead.

In one example, movement of the nozzle/printhead is controlled in accordance with a predetermined scheme while position of the printbed is fixed. In one example movement of the printbed is controlled in accordance with a predetermined scheme while the position of nozzle/printhead is fixed.

Figure 2:
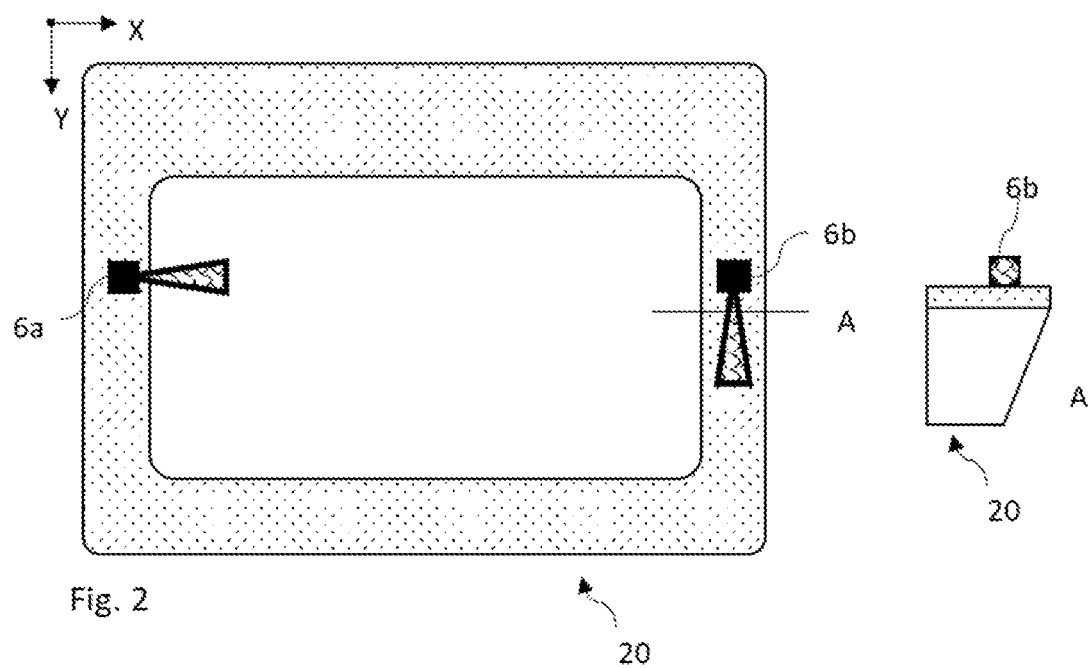
FIG. 2 shows the printbed of the biprinter in FIG. 1 from a top view (left) and a side view (right).

As shown in FIG. 1 and in FIG. 2, an ultrasonic sensor arrangement is arranged at the printbed 20. The ultrasonic sensor arrangement comprises a first sensor arrangement 6a arranged to provide a first ultrasound cone extending in a first direction (in the x-direction in FIG. 2) perpendicular to an extension of the nozzle 5 and a second sensor arrangement 6b arranged to provide a second ultrasound cone extending in a second direction (in the y-direction in FIG. 2) perpendicular to the extension of the nozzle 5. The first and the second sensor arrangements 6a, 6b are arranged to detect when the nozzle 5 has entered its ultrasound cone. The first and second directions preferably being perpendicular to each other as illustrated in FIG. 2.

The ultrasonic sensor arrangement may be used for calibrating the position of the at least one printhead/nozzle.

The first and second sensor arrangement 6a, 6b may each comprise an ultrasonic sensor, ultrasonic distance sensor, which measures distance by emitting sound and measuring the time-of-flight of sound reflected off objects in front of the sensor returning to the sensor. In case of multiple reflections at varying distances, the sensor detects only the nearest sound of reflection. Sound emitted can be seen as a cone. Ultrasonic distance sensor can detect small objects made from both plastic (such as polypropylene) and metal (such as stainless steel), why nozzles of different material may be used. For example may a sensor such as SICK UC4-13347 be used. Such a sensor has a measurement resolution of 100 μm or more and a repeatability of ±0.15%.

The ultrasonic sensors may be vertically arranged at the printbed such that the emitted sound cone is oriented in the x/y direction.

The ultrasonic sensor used may measure distances to an object up to 150 mm with a resolution of 200 um.

The ultrasonic sensors may be arranged anywhere at the printbed 20 as long as an ultrasound cone extending in the first/second direction perpendicular to the extension of the nozzle is formed.

The first and/or second sensor arrangement 6a, 6b may comprise an ultrasonic sensor and at least one solid surface (not shown) arranged to direct a beam from the sensor forming the cone extending in the first/second direction perpendicular to the extension of the nozzle.

The surface may e.g. be arranged at an angle of 45 degrees to the beam from the ultrasonic sensor. In this embodiment the ultrasonic sensor of the sensor arrangement could be oriented horizontally in the bioprinter 1 to make better use of available space at the printbed 20. Mounting the ultrasonic sensor horizontally requires the sound beam to be redirected to allow for the sound cone to be emitted in the x/y-direction.

Alternatively, the first and/or second sensor arrangement may comprise an ultrasonic sensor and a curved sound pipe (not illustrated) arranged to direct a beam from the sensor forming the cone extending in the first/second direction perpendicular to the extension of the nozzle.

Figure 3:
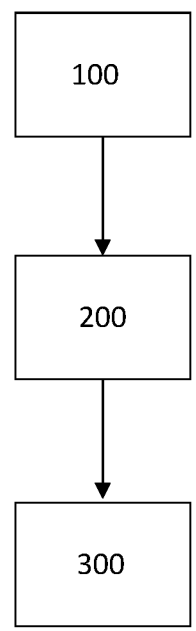
FIG. 3 illustrates schematically a method for calibration of a printhead/nozzle in a bioprinter.

The bioprinter further comprises a controller 7 arranged to control movement of the printhead/nozzle 4a, 4b, 4c; 5. The controller 7 is arranged to perform calibration, illustrated in FIG. 3, of the printhead/nozzle 4a, 4b, 4c; 5. This calibration comprises controlling 100 the printhead/nozzle in accordance with a calibration scheme, and to determine 200 a relation between the nozzle 5 and the first and second ultrasonic cones based on the detections by the first and second sensor arrangements 6a, 6b while the nozzle 5 is moving according to the calibration scheme, whereby a calibrated position of the printhead/nozzle at least in the first and second directions and preferably in the direction along the extension of the nozzle 5 can be obtained 300.

The controller 7 may further be arranged to control movement of the printhead/nozzle in accordance with the performed calibration.

Controlling the nozzle in accordance with a calibration scheme and determining a relation between the nozzle and the first and second ultrasonic cones based on the detections by the first and second sensor arrangements when the nozzle is moving according to the calibration scheme may comprise:

controlling the nozzle to move according to a position determination scheme controlling the nozzle in the second direction in relation to the first ultrasound cone so as to detect by means of the first ultrasonic sensor arrangement the location of the borders of the first ultrasound cone in the second direction, controlling the nozzle to move according to a position determination scheme controlling the nozzle in the first direction in relation to the second ultrasound cone, said position determination scheme being based on the location of the borders of the first ultrasound cone and a spatial relation between the first and the second ultrasonic sensor arrangements, so as to detect by means of the second ultrasonic sensor arrangement the location of the boarders of the second cone in the first direction, whereby the position of the nozzle in the first and second directions can be determined based on the locations of the borders of the first and second ultrasound cones.

Controlling the nozzle in accordance with a calibration scheme and determining a relation between the nozzle and the first and second ultrasonic cones based on the detections by the first and second sensor arrangements when the nozzle is moving according to the calibration scheme may further comprise controlling the nozzle to move according to a position determination scheme controlling the nozzle in the second direction in relation to the first ultrasound cone, said position determining scheme being based at least on the location of the borders of the second ultrasound cone and the spatial relation between the first and second ultrasonic sensor arrangements, so as to detect by means of the first ultrasonic sensor arrangement updated locations of the borders of the first ultrasound cone in the second direction, whereby the position of the nozzle in the first and second directions is determined based on the updated locations of the borders of the first ultrasound cones and the boarders of the second ultrasound cones.

The method may further comprise a step of determining a position of the nozzle in a direction extending substantially along the extension of the nozzle based on the knowledge of the position of the nozzle in the first and second directions.

The method may further comprise controlling the nozzle to a start position outside the first and second ultrasound cones in a direction along the extension of the nozzle, and controlling the nozzle to move from the start position according to a ultrasound cone finding pattern, so as to detects the first ultrasound cone, whereupon control according to the calibration scheme is started.

The invention claimed is:

1. A bioprinter comprising
at least one printhead, said printhead being provided with a nozzle,
a printbed onto which the printhead is arranged to print an ink,
an ultrasonic sensor arrangement arranged at the printbed, said ultrasonic sensor arrangement comprising a first sensor arrangement being arranged to provide a first ultrasound cone extending in a first direction perpendicular to an extension of the nozzle and a second sensor arrangement being arranged to provide a second ultrasound cone extending in a second direction perpendicular to the extension of the nozzle, wherein the first and the second sensor arrangement are arranged to detect when the nozzle has entered its ultrasound cone, the first and second directions being perpendicular to each other, and
a controller arranged to control movement of the printhead, said controller being arranged to perform calibration of the printhead, said calibration comprising controlling the printhead in accordance with a calibration scheme, and to determine a relation between the printhead and the first and second ultrasonic cones based on the detections by the first and second sensor arrangements while the nozzle is moving according to the calibration scheme, wherein in said calibration, the controller is arranged to control the nozzle to move according to a position determination scheme controlling the nozzle in the second direction in relation to the first ultrasound cone, wherein the first ultrasonic sensor arrangement is arranged to detect a location of a border of the first ultrasound cone in the second direction, wherein the controller is arranged to control the nozzle to move according to a position determination scheme controlling the nozzle in the first direction in relation to the second ultrasound cone, said position determination scheme being based on the location of the borders of the first ultrasound cone and a spatial relation between the first and the second ultrasonic sensor arrangements, wherein the second ultrasonic sensor arrangement is arranged to detect a location of a border of the second ultrasound cone in the first direction, whereby the position of the nozzle in the first and second directions can be determined based on the locations of the borders of the first and second ultrasound cones, whereby a calibrated position of the printhead at least in the first and second directions and in the direction along the extension of the nozzle can be obtained, and said controller further being arranged to control movement of the printhead in accordance with the performed calibration.

2. The bioprinter of claim 1, wherein the first and/or second sensor arrangement each comprises an ultrasonic sensor and at least one solid surface arranged to direct a beam from the sensor forming the ultrasound cone extending in the first/second direction perpendicular to the extension of the nozzle.

3. Method for calibration of a printhead in a bioprinter, the printhead being provided with a nozzle, the bioprinter further comprising a printbed onto which the printhead is arranged to print an ink, and an ultrasonic sensor arrangement arranged at the printbed, said ultrasonic sensor arrangement comprising a first sensor arrangement being arranged to provide a first ultrasound cone extending in a first direction perpendicular to an extension of the nozzle and a second sensor arrangement being arranged to provide a second ultrasound cone extending in a second direction perpendicular to the extension of the nozzle, wherein the first and the second sensor arrangement detects when the nozzle has entered its ultrasound cone, the first and second directions being perpendicular to each other, said method comprising the steps of controlling the printhead in accordance with a calibration scheme and determining a relation between the nozzle and the first and second ultrasonic cones based on the detections by the first and second sensor arrangements when the printhead is moving according to the calibration scheme, wherein the nozzle is controlled to move according to a position determination scheme controlling the nozzle in the second direction in relation to the first ultrasound cone so as to detect by means of the first ultrasonic sensor arrangement a location of a border of the first ultrasound cone in the second direction, and the nozzle is controlled to move according to a position determination scheme controlling the nozzle in the first direction in relation to the second ultrasound cone, said position determination scheme being based on the location of the borders of the first ultrasound cone and a spatial relation between the first and the second ultrasonic sensor arrangements, so as to detect by means of the second ultrasonic sensor arrangement a location of a border of the second ultrasound cone in the first direction, whereby the position of the nozzle in the first and second directions can be determined based on the locations of the borders of the first and second ultrasound cones, whereby a calibrated position of the printhead at least in the first and second directions and in the direction along the extension of the nozzle can be obtained.

4. The method according to claim 3, wherein controlling the nozzle in accordance with a calibration scheme and determining a relation between the nozzle and the first and second ultrasonic cones based on the detections by the first and second sensor arrangements when the nozzle is moving according to the calibration scheme further comprises controlling the nozzle to move according to a position determination scheme controlling the nozzle in the second direction in relation to the first ultrasound cone, said position determining scheme being based at least on a location of the borders of the second ultrasound cone and the spatial relation between the first and second ultrasonic sensor arrangements, so as to detect by means of the first ultrasonic sensor arrangement updated locations of the borders of the first ultrasound cone in the second direction, whereby the position of the nozzle in the first and second directions is determined based on the updated locations of the borders of the first ultrasound cone and the location of the borders of the second ultrasound cone.

5. The method according to claim 3, further comprising a step of determining a position of the nozzle in a direction extending substantially along the extension of the nozzle based on a knowledge of the position of the nozzle in the first and second directions.

6. The method according to claim 3, further comprising controlling the nozzle to a start position outside the first and second ultrasound cones in a direction along the extension of the nozzle, and controlling the nozzle to move from the start position according to an ultrasound cone finding pattern, so as to detect the first ultrasound cone, whereupon control according to the calibration scheme is started.

* * * * *